United States Patent [19]

Bohanan

[11] Patent Number: 5,395,445
[45] Date of Patent: Mar. 7, 1995

[54] METHOD AND APPARATUS FOR DETECTING FINGERPRINTS ON SKIN

[76] Inventor: Arthur M. Bohanan, Criminalistics Unit, City of Knoxville Police Department, Box 3610, Knoxville, Tenn. 37927

[21] Appl. No.: 64,955

[22] Filed: May 20, 1993

[51] Int. Cl.⁶ ................................................ B41K 1/00
[52] U.S. Cl. ................................... 118/31.5; 118/720; 118/724; 118/726; 427/1; 427/145; 427/248.1
[58] Field of Search ................ 427/1, 145, 248.1; 118/31.5, 720, 724, 726

[56] References Cited

U.S. PATENT DOCUMENTS

| | | | |
|---|---|---|---|
| 4,260,645 | 4/1981 | Kerr et al. | 427/1 |
| 4,297,383 | 10/1981 | Bourdon | 427/1 |
| 4,407,842 | 10/1983 | Shepard | 427/1 |
| 4,461,235 | 7/1984 | Morton | 118/31.5 |
| 4,556,579 | 12/1985 | Lowell | 427/1 |
| 4,613,515 | 9/1986 | Reggio | 427/1 |
| 4,700,657 | 10/1987 | Butland | 427/1 |
| 4,806,380 | 2/1989 | Sato et al. | 427/1 |
| 4,882,195 | 11/1989 | Butland | 427/1 |
| 5,194,289 | 3/1993 | Butland | 427/1 |

FOREIGN PATENT DOCUMENTS

| | | | |
|---|---|---|---|
| 0258938 | 8/1988 | Germany | 42/7 |
| 2268744 | 11/1990 | Japan | 427/1 |

*Primary Examiner*—Janyce Bell
*Attorney, Agent, or Firm*—Luedeka, Neely & Graham

[57] ABSTRACT

A method for rendering latent fingerprints at a site on a portion of skin detectable. The method comprises the steps of forming a cyanoacrylate vapor from a cyanoacrylate, conducting the cyanoacrylate vapor to the site on a portion of skin, and applying the cyanoacrylate vapor to the site at a sufficient concentration for a period of time of between about 15 seconds and about 30 seconds sufficient to deposit between about 0.31 mg/cm² and about 0.78 mg/cm² of the cyanoacrylate on the portion of skin. The present invention also provides an apparatus for rendering latent fingerprints at a site on a portion of skin detectable.

1 Claim, 1 Drawing Sheet

METHOD AND APPARATUS FOR DETECTING FINGERPRINTS ON SKIN

FIELD OF THE INVENTION

The present invention relates to methods and apparatus for rendering latent fingerprints on skin detectable.

BACKGROUND OF THE INVENTION

Developing identifiable latent fingerprints from human skin has been a constant frustration to police examiners for a number of years. Past research has been unable to develop a reliable technique for fingerprinting the skin of cadavers.

Many murder victims have had useable latent prints on their bodies but existing techniques failed to recover them for use in identifying any suspects. Generally, the attempts using techniques of the prior art give results between no results and an outline of the fingers or hands.

In the prior art, a number of methods of developing fingerprints have been disclosed. The purpose of most of these methods is to permit fingerprints to be visually displayed on an object without disturbing the fingerprint by means of the development procedure. Many of the prior art methods require that the fingerprints be brushed with a powder or soaked in a solution or otherwise dealt with in a manner which might smudge or harm the latent fingerprints to be developed.

The most commonly used technique for developing latent fingerprints is the dusting method which involves covering a surface or object with a fine powder such as ground carbon or pumice. Other methods for developing latent fingerprints include treating a surface with the chemical ninhydrin; however, this chemical is difficult to use and is highly explosive. Still other methods for developing latent fingerprints include the fuming of objects with iodine gas, and the dipping of objects in silver nitrate. These methods are relatively messy, the developed fingerprints fade quickly, and surfaces of the objects on which latent fingerprints are sought may be damaged. Laser light can be used to expose and outline fingerprints. However, it is inconvenient and expensive to use as it requires a relatively heavy Argon ion laser unit.

Many apparatus have been developed for dealing with the problem of rendering latent fingerprints on objects detectable. However, it has been difficult to apply such techniques to render latent fingerprints detectable on human skin.

It is often necessary, for example, in the case of a murder victim, to render latent fingerprints detectable upon the skin of a victim. Often such victims are not discovered for days or even weeks after the crime and detection of the fingerprints is quite difficult.

Several references in the prior art teach the use of cyanoacrylate vapors for treating objects such that latent fingerprints become detectable upon treatment with appropriate dusting powders. However, the methods of these references are often time consuming, taking upwards from 12 hours to render a latent fingerprint detectable. In addition, the systems disclosed in these references are often inappropriate for use with fingerprints on human skin. Such systems require the immersion of an object in the vapors of the cyanoacrylate for long periods of time. This is often difficult in the case of human bodies.

Therefore, it is an object of the present invention to provide a method and apparatus for rendering latent fingerprints on human skin detectable in a period of time less than one minute.

It is another object of the invention to provide an apparatus which is sufficiently portable such that the apparatus may be easily transported to and from a crime scene for use in rendering latent fingerprints on skin detectable.

Further study of the specification, Figure and Example will lead the practitioner to additional objects and advantages of the present invention.

SUMMARY OF THE INVENTION

The present invention provides a method for rendering latent fingerprints at a site on a portion of skin detectable. The method comprises the steps of forming a cyanoacrylate vapor from a cyanoacrylate, conducting the cyanoacrylate vapor to the site on a portion of skin, and applying the cyanoacrylate vapor to the site at a sufficient concentration for a period of time of between about 15 seconds and about 30 seconds sufficient to deposit between about 0.31 $mg/cm^2$ and about 0.78 $mg/cm^2$ of the cyanoacrylate on the portion of skin. In a preferred embodiment of the invention, the step of forming the cyanoacrylate vapor comprises heating a liquid source of cyanoacrylate at a temperature of between about 190° C. and about 220° C., or, more preferably, the heating occurs at a temperature of about 205° C.

The present invention also provides an apparatus for rendering latent fingerprints at a site on a portion of skin detectable. The apparatus comprises means for producing a cyanoacrylate vapor from a cyanoacrylate, and means for conducting the cyanoacrylate vapor to the site at a sufficient concentration for a period of time of between about 15 seconds and about 30 seconds sufficient to deposit between about 0.31 $mg/cm^2$ and about 0.78 $mg/cm^2$ of the cyanoacrylate on the portion of skin.

Preferably, the means for producing the cyanoacrylate vapor further comprises a heater having at least one surface capable of being controllably heated to a continuous temperature of between about 190° C. and about 220° C., a container for holding an amount of the cyanoacrylate and for being placed in contact with the at least one surface of the heater, and a vessel for containing the heater, the container and the cyanoacrylate vapors. The cyanoacrylate is placed in the container which is in contact with the at least one surface of the heater and the at least one surface of the heater is raised in temperature to between about 190° C. and about 220° C. In a further preferred embodiment of the invention, the heater has at least one surface capable of being controllably heated to a continuous temperature of about 205° C.

It is also preferred that the means for conducting the cyanoacrylate vapor further comprises at least one conduit for conducting the cyanoacrylate vapors from the vessel to the site on a portion of skin, a coupling for connecting the at least one conduit to the vessel, and means for forcing the cyanoacrylate vapor from the vessel, into the at least one conduit, and to the site on a portion of skin. In another preferred embodiment of the apparatus according to the present invention, the means for forcing the vapor into the conduit and from the vessel comprises at least one fan capable of being adjusted so that the volume of air that is forced by the at least one fan is controllably variable.

The present invention also provides for an apparatus for rendering latent fingerprints at a site on a portion of skin detectable. The apparatus comprises a first vessel having an inside and an outside, and having at least one first port wherein the inside of the first vessel is in fluid communication with the atmosphere surrounding the first vessel through the at least one first port and having at least one second port and at least one fan situated inside the first vessel. There is also a second vessel having an inside and an outside, and having at least one first port placed substantially in association with the at least one second port of the first vessel wherein the inside of the first vessel is in fluid communication with the inside of the second vessel through the at least one second port of the first vessel and the at least one first port of the second vessel. Heating means having at least one heating element which is adjustable to produce a temperature of between about 190° C. and about 220° C. are also provided, wherein the heating means is situated inside the second vessel. A container for holding an amount of a cyanoacrylate and for being placed in contact with the at least one surface of the heater is also situated inside the second vessel. There is at least one conduit having an inside and an outside, and each of the at least one conduit having a distal end and a proximal end, wherein the proximal end of the at least one conduit is attached to the second vessel substantially in association with the at least one second port of the second vessel, and wherein the inside of the at least one conduit is in fluid communication with the inside of the second vessel. Further, there are application means having an inside and an outside and at least one first port which is substantially in association with the distal end of the at least one conduit. Thus, the inside of the application means is in fluid communication with the inside of the at least one conduit. The application means also has at least one second port wherein the inside of the application means is in fluid communication with the atmosphere surrounding the outside of the application means. Further, the application means has an outlet with a circumference to substantially circumscribe the site on a portion of skin.

The apparatus according to the invention operates such that a portion of cyanoacrylate is placed in the container situated in the second vessel and the heating means is adjusted to a temperature of between about 190° C. and about 220° C. wherein a vapor of the cyanoacrylate is produced, and the at least one fan situated in the first vessel is energized to bring air in from the atmosphere surrounding the first vessel through the at least one first port in the first vessel. The at least one fan sends the air out of the first vessel through the at least one second port of the first vessel and the at least one first port of the second vessel. The vapor of the cyanoacrylate is entrained in the air in the second vessel and the air with the entrained vapor is sent from the second vessel into the at least one conduit through the at least one second port in the second vessel and the proximal end of the conduit. Thence the air with the entrained vapor is sent to the application means from the distal end of the at least one conduit and the at least one first port in the application means. The application means is placed in contact with the site on a portion of skin, and the air with the entrained vapor is in contact with the portion of skin through the outlet of the application means and the air with the entrained vapor flows out of the application means through the at least one second port of the application means to the atmosphere surrounding the application means. Thus, the skin is exposed to the vapor for a period of time sufficient to render latent fingerprints on the portion of skin detectable.

DETAILED DESCRIPTION OF THE INVENTION

Figure 1:
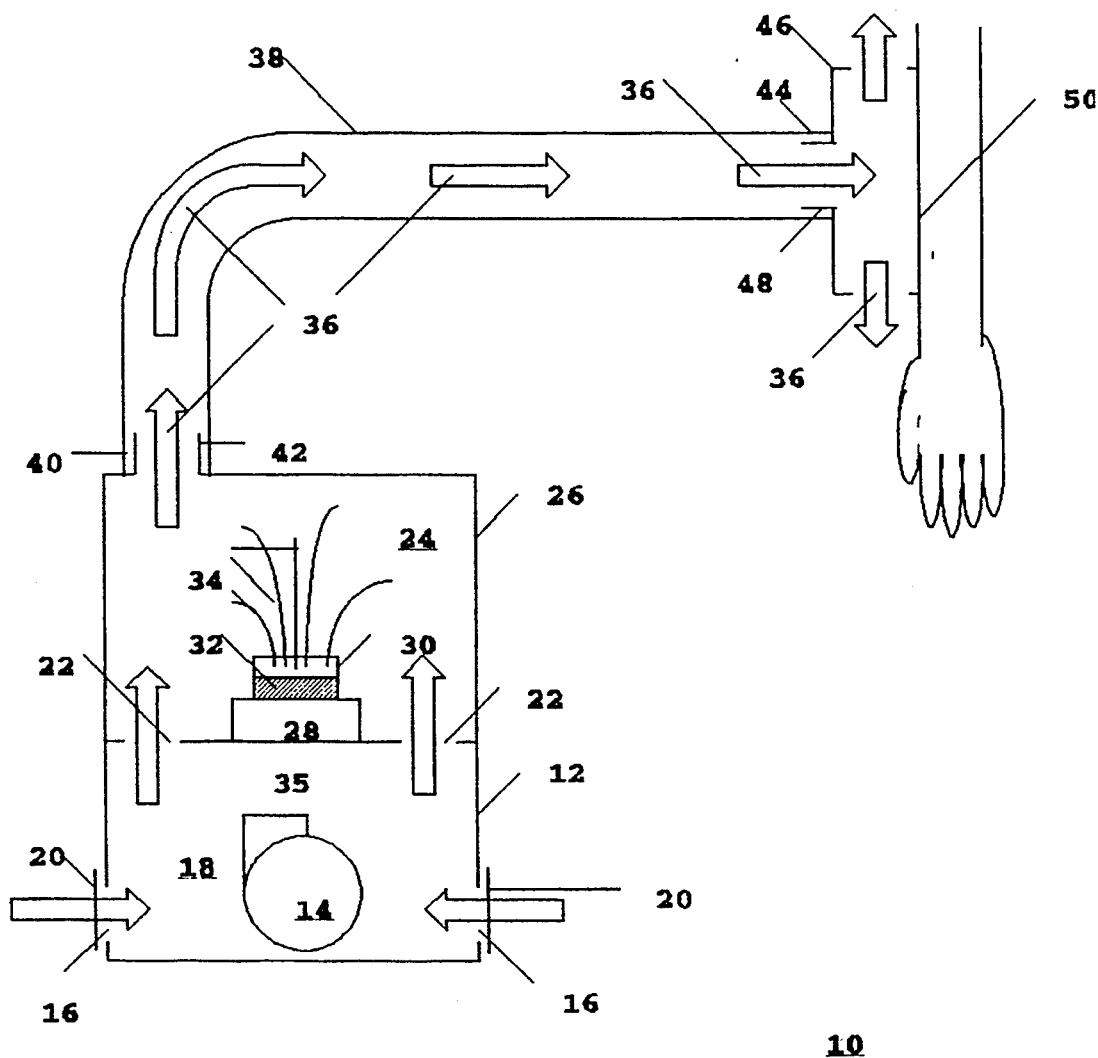
FIG. 1 is a cross-sectional schematic drawing of an apparatus according to the present invention for rendering latent fingerprints on skin detectable.

In order to understand the present invention, reference should be made to the following description of a preferred embodiment of the invention. Referring to FIG. 1, there is shown in FIG. 1 an apparatus 10 for rendering latent fingerprints on skin detectable. The apparatus 10 comprises a fan housing 12 which contains a fan 14 for drawing air from the outside of the fan housing 12 through the openings 16 and into the interior 18 of the fan housing 12. The amount of air drawn through the opening 16 by the fan 14 is adjustable by positioning the damper 20 to restrict the amount of air capable of flowing into the interior 18 of the fan housing 12. The air in the interior 18 is then forced through the openings 22 into the interior 24 of a heater chamber 26. The heater chamber 26 contains a heater 28 which is capable of being adjusted to a temperature of between about 190° C. and 220° C. A container 30 is placed on the heater 28 in such a way that the bottom of the container 30 is in contact with a heating element of the heater 28. A liquid cyanoacrylate 32 is placed in the container 30 as the container is heated up to a temperature of between about 190° C. and 220° C. Fumes 34 of the liquid cyanoacrylate 32 are released into the interior 24 of the heater chamber 26. The fumes 34 become entrained in the air 35 flowing into the interior 24 of the heater chamber 26 from the interior 18 of the fan housing 12, forming vapor entrained air 36. A hose 38 is attached at a proximal end 40 to the heater chamber 26 at a connector 42. The distal end 44 of the hose 38 is attached to an application means 46 at a connector 48. The vapor entrained air 36 travels from the interior 24 of the heater chamber 26 through the hose 38 and into the application means 46. There, the vapor entrained air 36 comes in contact with skin 50 and flows out of the application means 46 through vents 52.

In operation, several drops of the liquid cyanoacrylate 32 are placed in the container 30 prior to bringing the heater 28 up to temperature. At that point, the heater chamber 26 is open to allow access to the container 30 by the operator. The heater chamber 26 is closed and the hose 38 is attached to the application means 46 and the heater chamber 26. The heater 28 is adjusted to a temperature of between about 190° C. and about 220° C. with a most preferred temperature of about 205° C. While the heater 28 is coming to temperature, the fan 14 is energized and the damper 20 is adjusted to allow a flow of vapor entrained air 36 through the application means 46 such that between about 0.31 mg/cm$^2$ and about 0.78 mg/cm$^2$ of cyanoacrylate is deposited on the skin in a period of time of from about 15 seconds to about 30 seconds. The application means 46 is placed on the skin 50 for a period of a time of between 15 seconds and about 30 seconds and then removed from the skin. At that point, the skin is dusted for fingerprints using anyone of a number of conventional powders for detecting fingerprints.

In order to provide a further understanding of the invention, the following examples illustrate, but do not limit the invention.

EXAMPLE I

Fingerprints were placed upon the body of a forty-four year old white male. These prints included perspiration prints as well as oily prints. The perspiration prints were placed on the body by a person after first washing their hands, waiting a period of time of about 10 minutes and then touching the body in designated areas. The person then rubbed their hands on their face and applied their hands to the body in another designated area.

The apparatus as previously herein described was prepared for rendering the fingerprints detectable. Liquid cyanoacrylate was placed in the container and the heater was brought to a temperature of about 205° C. The fan was turned on and, after approximately 2 minutes, the application means was applied to the body a number of times for periods of between about 5 seconds to about 3 minutes. After exposure of the skin to the cyanoacrylate vapors for the period of time designated, the application means was removed and the skin was treated with a standard fingerprint powder such as black magnetic powder, a mixture of black magnetic powder and copier toner, and copper magnetic powder. No latent prints of value were developed on areas of skin where perspiration prints had been deposited. However, latent prints of value were developed in those areas where oily prints had been deposited. The prints rendered on skin which was treated with the cyanoacrylate vapor for less than 15 seconds were of poor quality, as were those prints on areas of skin treated greater than 30 seconds. The best quality latent prints were developed by exposing the skin to cyanoacrylate vapors using an apparatus of the present invention for a period of time of between about 15 and about 30 seconds.

Excellent quality latent prints were developed with black magnetic powder, as well as with various fluorescent magnetic and regular fluorescent powders. These latent prints were developed approximately 3 hours after the skin was touched although the method is useful for rendering latent fingerprints detectable days after the skin was touched.

Thus, the present invention provides a method and apparatus for rendering latent fingerprints on skin detectable in periods of time of less than about 1 minute. In addition, the present invention provides an apparatus which is sufficiently portable for transport to and from a crime scene wherein the apparatus is used to render latent fingerprints on skin detectable.

The foregoing is considered as illustrating only the principals of the invention. Since numerous modifications and changes will readily occur to those skilled in the art, it is not intended to limit the invention to the exact materials and ratios disclosed, and accordingly, all suitable modifications and equivalents may be resorted to, falling within the scope of the invention.

Those aspects of the invention considered to be new are set forth in the attached claims.

What is claimed is:

1. An apparatus for rendering latent fingerprints at a site on a portion of skin detectable, the apparatus comprising:

a first vessel having an inside and an outside, and having at least one first port wherein the inside of the first vessel is in fluid communication with the atmosphere surrounding the first vessel through the at least one first port, and having at least one second port;

at least one fan situated inside the first vessel;

a second vessel having an inside and an outside, and having at least one first port placed substantially in association with the at least one second port of the first vessel wherein the inside of the first vessel is in fluid communication with the inside of the second vessel through the at least one second port of the first vessel and the at least one first port of the second vessel;

heating means having at least one heating element which is adjustable to produce a temperature of between about 190° C. and about 220° C., wherein the heating means is situated inside the second vessel;

a container for holding an amount of a cyanoacrylate and for being placed in contact with the at least one surface of the heater, wherein the container is situated inside the second vessel;

at least one hose having an inside and an outside, and each of the at least one hose having a distal end and a proximal end, wherein the proximal end of the at least one hose is attached to the second vessel substantially in association with the at least one second port of the second vessel, and wherein the inside of the at least one hose is in fluid communication with the inside of the second vessel; and application means having an inside and an outside, and the application means having at least one first port which is substantially in association with the distal end of the at least one hose wherein the inside of the application means is in fluid communication with the inside of the at least one hose, and the application means having at least one second port wherein the inside of the application means is in fluid communication with the atmosphere surrounding the outside of the application means, and the application means having an outlet with a circumference to substantially circumscribe the site on a portion of skin, such that a portion of cyanoacrylate is placed in the container situated in the second vessel and the heating means is adjusted to a temperature of between about 190° C. and about 220° C., wherein a vapor of the cyanoacrylate is produced, and the at least one fan situated in the first vessel is energized to bring air in from the atmosphere surrounding the first vessel through the at least one first port in the first vessel, and the at least one fan sends the air out of the first vessel through the at least one second port of the first vessel and the at least one first port of the second vessel, and the vapor of the cyanoacrylate is entrained in the air in the second vessel, and the air with the entrained vapor is sent from the second vessel into the at least one hose through the at least one second port in the second vessel and the proximal end of the hose, and thence the air with the entrained vapor is sent to the application means from the distal end of the at least one hose and the at least one first port in the application means, further such that the application means is placed in contact with the site on a portion of skin, and the air with the entrained vapor is in contact with the portion of skin through the outlet of the application means and the air with the entrained vapor flows out of the application means through the at least one second port of the application means to the atmosphere surrounding the application means, and wherein the skin is exposed to the vapor for a period of time sufficient to render latent fingerprints on the portion of skin detectable.

* * * * *